(12) United States Patent
Hodgson

(10) Patent No.: US 7,640,644 B2
(45) Date of Patent: Jan. 5, 2010

(54) METHOD FOR FLUID-SHAPING OF SHEET METAL

(75) Inventor: Jan Hodgson, Troisdorf (DE)

(73) Assignee: Emitec Gesellschaft fuer Emissionstechnologie mbH, Lohmar (DE)

( * ) Notice: Subject to any disclaimer, the term of this patent is extended or adjusted under 35 U.S.C. 154(b) by 173 days.

(21) Appl. No.: 11/483,701

(22) Filed: Jul. 10, 2006

(65) Prior Publication Data

US 2006/0288556 A1 Dec. 28, 2006

Related U.S. Application Data

(63) Continuation of application No. PCT/EP2004/014822, filed on Dec. 30, 2004.

(30) Foreign Application Priority Data

Jan. 9, 2004 (DE) .................. 10 2004 001 418

(51) Int. Cl.
*B23P 17/00* (2006.01)
(52) U.S. Cl. ..................................... 29/421.1
(58) Field of Classification Search ............... 29/421.1, 29/557, 432, 890.08
See application file for complete search history.

(56) References Cited

U.S. PATENT DOCUMENTS

| 4,273,681 A | 6/1981 | Nonnenmann |
| 4,832,998 A | 5/1989 | Cyron |
| 5,916,317 A | 6/1999 | Willoughby et al. |

FOREIGN PATENT DOCUMENTS

| DE | 29 02 779 A1 | 7/1980 |
| DE | 29 07 420 B2 | 8/1980 |
| DE | 42 30 143 A1 | 3/1994 |
| DE | 198 03 782 A1 | 8/1999 |
| DE | 100 26 679 A1 | 12/2001 |
| DE | 100 59 055 A1 | 6/2002 |
| EP | 0 245 737 B1 | 11/1987 |
| GB | 1 499 829 | 2/1978 |
| WO | 90/03220 | 4/1990 |
| WO | 91/01178 | 2/1991 |

*Primary Examiner*—John C Hong
(74) *Attorney, Agent, or Firm*—Laurence A. Greenberg; Werner H. Stemer; Ralph E. Locher

(57) ABSTRACT

A method for manufacturing an exhaust gas treatment component having at least one structured piece of sheet metal, includes shaping the at least one piece of sheet metal with at least one fluid stream. A device for producing a structured piece of sheet metal is also provided.

11 Claims, 3 Drawing Sheets

FIG. 5A
FIG. 5B
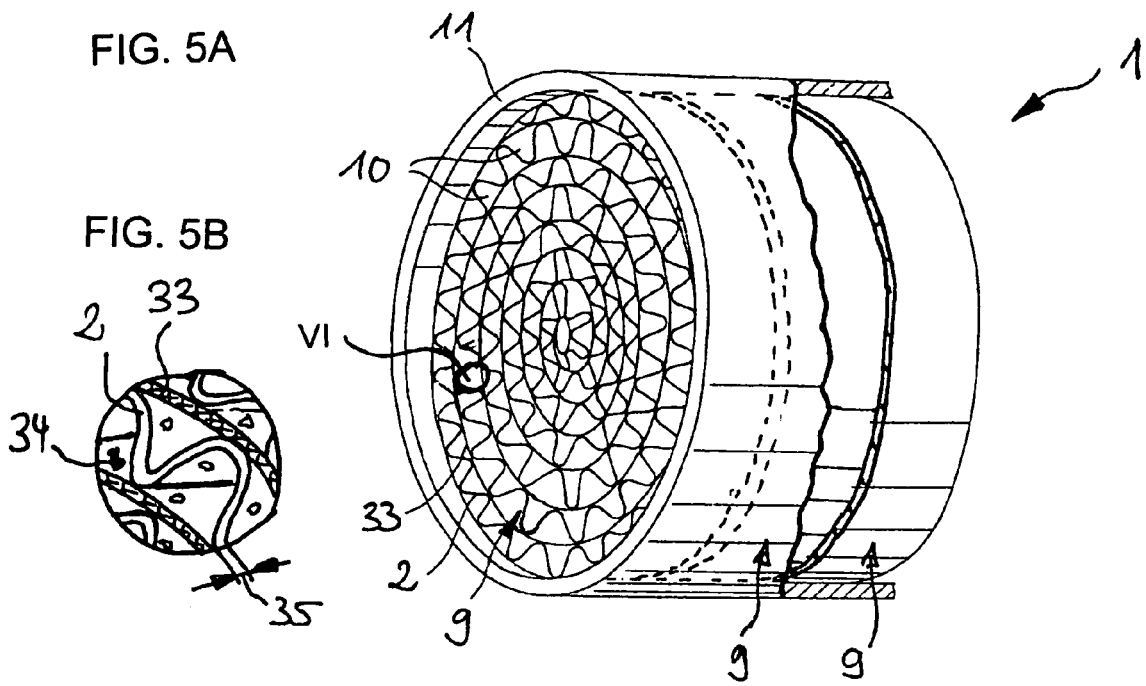
FIG. 6A
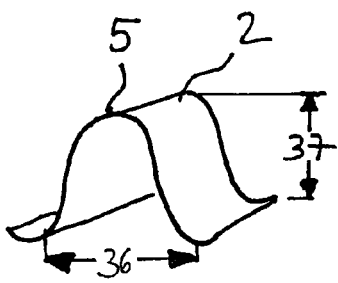
FIG. 6B
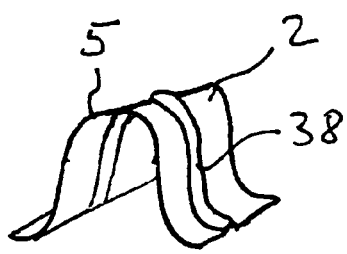
FIG. 6C
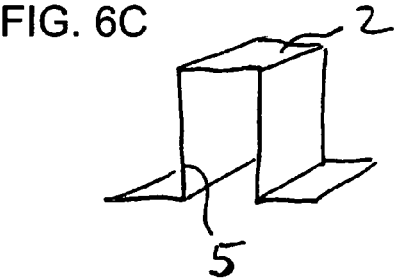
FIG. 6D
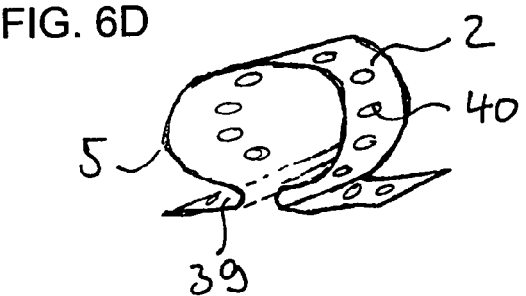

METHOD FOR FLUID-SHAPING OF SHEET METAL

CROSS-REFERENCE TO RELATED APPLICATION

This is a continuation, under 35 U.S.C. §120, of copending International Application No. PCT/EP2004/014822, filed Dec. 30, 2004, which designated the United States; this application also claims the priority, under 35 U.S.C. §119, of German Patent Application 10 2004 001 418.3, filed Jan. 9, 2004; the prior applications are herewith incorporated by reference in their entirety.

BACKGROUND OF THE INVENTION

Field of the Invention

The invention relates to a method for manufacturing an exhaust gas component which has at least one structured piece of sheet metal. The invention also relates to a device for producing a structured piece of sheet metal.

Exhaust gas treatment components can be divided in terms of their structure into basically two different variants: extruded and assembled. In the exhaust gas treatment components which are manufactured by using the extrusion method, a ceramic or metallic mass is formed in a state which can be shaped according to the desired shape of the exhaust gas treatment component, and subsequently hardened. In the case of exhaust gas treatment components which are composed of a plurality of individual parts, the individual parts (pieces of sheet metal, mats, sensors, connections, housings etc.) are generally manufactured individually and subsequently assembled before they are then connected to one another. The invention relates primarily to the last-mentioned variant of an exhaust gas treatment component.

The general term exhaust gas treatment component is understood to apply to all components which are currently used in mobile exhaust systems. That includes in particular catalytic converters, filters, particle traps, heat exchangers, mixers, adsorbers and hybrid forms of such devices.

The exhaust gas treatment components which are relevant in such a case have at least one structured piece of sheet metal. "Sheet metal" is to be understood herein as a generic term for metal strips, sheet metal plates, etc. The sheet metal is preferably composed of a high temperature-proof and corrosion resistant material. In particular, it is based on iron, with at least one of the elements from the group chromium, nickel or aluminum being additionally present. The sheet metal may either be what is referred to as heavy sheet metal or what is referred to as light sheet metal (which has been soft annealed once more after hardening). The thickness of the sheet metal is preferably in a range of less than 150 μm, in particular less than 110 μm and preferably in a range of from 20 μm to 80 μm.

In an exhaust gas treatment component, such a structured piece of sheet metal generally fulfills the function of at least partially limiting flow paths or passages through the exhaust gas treatment component. For that purpose, the structured piece of sheet metal is butted against itself and/or further pieces of sheet metal and possibly connected. The resulting flow paths or passages have significant effects on the method of operation of the exhaust gas treatment component. For example, the surface which is provided per volume of the exhaust gas treatment component, the ram or head pressure resulting when there is a flow through the exhaust gas treatment component and the mixture of component streams in the interior of the exhaust gas treatment component, etc. are decisively influenced. In that context, the different requirements often contradict one another so that improving one property causes another to become worse. For that reason, significant research activities have already focused on optimizing the structural shape of the piece of sheet metal. It has become apparent, for example, that the resulting flow paths or passages should be made relatively narrow with steep edges. As a result thereof, the structure of the pieces of sheet metal no longer necessarily corresponds approximately to a normal sinusoidal shape but instead has a different structure. In addition, it has become apparent that the provision of different structures, for example a macrostructure and a microstructure, is particularly advantageous for the flow behavior.

The requirements mentioned above result in a situation in which particular attention also has to be paid to the fabrication of such pieces of sheet metal in order to form a structure. Such pieces of sheet metal are usually fed in the form of a strip into roll forms which intermesh with one another and which deform or shape the piece of sheet metal. Due to the fact that different parameters for the structure have to be respectively produced for different applications of the piece of sheet metal, a very large number of expensive tools which are costly to manufacture are necessary when manufacturing with roll forms. In addition, it is necessary to take into account the fact that when the relatively thin pieces of sheet metal are led through the roll forms which engage one in the other, the material may be damaged since the piece of sheet metal is partially drawn over a tooth of the roll form. Such reduction in the thickness or formation of fractures in the piece of sheet metal can lead to premature failure of the exhaust gas treatment component because those imperfections ultimately constitute a point of attack for the high thermal and dynamic forces which occur, for example in the exhaust system of a motor vehicle.

SUMMARY OF THE INVENTION

It is accordingly an object of the invention to provide a method and a device for fluid-shaping of sheet metal, which overcomes the hereinafore-mentioned disadvantages of the heretofore-known methods and devices of this general type and in which a method for manufacturing structured pieces of sheet metal can be carried out particularly easily, can be used in a versatile way and is variable and economical. At the same time, the requirements made of series production of structured pieces of sheet metal are to be fulfilled. In addition, the device for manufacturing such structured pieces of sheet metal should have a simple construction and be cost-effective with respect to its manufacture and/or operation.

With the foregoing and other objects in view there is provided, in accordance with the invention, a method for manufacturing an exhaust gas treatment component. The method comprises providing at least one piece of sheet metal and structuring the at least one piece of sheet metal by shaping with at least one fluid stream.

"Shaping" is understood in particular to mean pure flexural stressing of the piece of sheet metal. The reason for this is the fluid stream which impinges on the surface of the piece of sheet metal. The fluid stream shapes, reshapes or works the piece of sheet metal until the angle at which it impinges on the surface of the piece of sheet metal becomes too acute or the section of the piece of sheet metal to be shaped is pressed completely into a countermold. The fluid stream is formed in this case as a function of the structure to be produced, the fluid used, the tool and/or the material of the sheet metal. The fluid stream is also preferably regulated as a function of at least one of the factors mentioned above by adapting at least one of the following parameters: pressure, mass flow, flow rate, shape, shaping force. In this context, at least one of the following parameters is preferably selected:

| | |
|---|---|
| pressure: | greater than 50 bar, in particular 60 to 100 bar; |
| volume flow: | greater than 10 l/min per 10 mm nozzle gap width, in particular between 15 and 30 l/min; |
| flow rate: | higher than 100 m/s, in particular higher than 150 m/s; |
| shape: | conical, linear or gap-shaped, in particular converging; |
| shaping force: | approximately 350 N to 500 N. |

The above values relate in particular to non-soft-annealed pieces of sheet metal (referred to as "hard strip") with a sheet metal thickness of approximately 50 μm and a width of 75 mm, with the hard strip being shaped simultaneously and uniformly over the entire width. Due to the fact that the above parameters are heavily dependent on the fluid distribution device which produces such a fluid stream, the specified values can, under certain circumstances, also differ with different devices for carrying out the method.

In accordance with another mode of the invention, the at least one fluid stream has at least one of the following components: water, oil, particles, additives. The use of a fluid stream which is composed substantially of water has advantages in particular in terms of environmental aspects or cost-effective disposal and cleaning of the fluid. In other application areas, for example at high degrees of shaping, it may also be advantageous to use a fluid stream which is predominantly composed of oil. In addition, it is possible for the fluid stream to have particles added to it which contribute, for example, to the surface treatment of the sheet metal (induction of inherent stress, cleaning, etc.). In addition, it is also possible to add additives which include in particular chemical substances which serve, for example, to clean the surface of the sheet metal, to clean the fluid distribution device and/or further components of the device for manufacturing the structured piece of sheet metal.

In accordance with a further mode of the invention, the method takes place intermittently. This is aimed in particular at the forward feed of the sheet metal during processing. Although the method can also be carried out continuously, an intermittent forward feed of the sheet metal is preferred. The supply of fluid or the formation of the fluid stream which is necessary for shaping can be made dependent on the intermittent forward feed of the sheet metal so that the formation of the fluid stream also has the frequency of the forward feed superimposed thereon. However, it is also possible for the fluid stream to be maintained continuously or uninterruptedly during the intermittent forward feed of the sheet metal.

Due to the fact that the method described herein is often to be used within the scope of series fabrication in the motor vehicle supplier industry, a forward feed of the sheet metal of at least 10 m/min, in particular at least 12 m/min and preferably at least 15 m/min is set. Since the structures to be produced generally repeat according to a pattern and in each case a structure or a structured section is produced by the fluid stream when the piece of sheet metal is stationary, corresponding clocking frequencies come about. If, for example, a sheet metal blank is processed by at least one fluid stream in order to produce a structured section with a length, for example, of 5 mm, a clocking frequency of approximately 40 Hz [1/second] occurs, with a forward feed rate of the piece of sheet metal of approximately 12 m/min having been assumed. Methods which are suitable for series fabrication have a clocking frequency of at least 20 Hz. This method is advantageously to be operated with a forward feed speed of the piece of sheet metal of at least 20 m/min, and in particular even of over 50 m/min.

In accordance with an added mode of the invention, before the shaping, the at least one piece of sheet metal is subjected to a method step including the cutting of sheet metal. The cutting of sheet metal can be carried out, for example, by one of the fabrication methods of cutting, punching or else by high-energy irradiation with a medium (water, abrasive agents, lasers, etc.). In this context cutting is not to be understood to mean complete disconnection of pieces of sheet metal from a strip or coil but rather instead the cutting of sheet metal in specific internal regions of the piece of sheet metal. As a result, openings, slits or other cutouts are formed in the (still smooth) piece of sheet metal. Such cuts are positioned, if appropriate, with respect to the shaping of the sheet metal which is carried out subsequently, so that defined protrusions can be formed in the sheet metal. Furthermore, it is also possible for these openings to be used for the purposes of saving material, as a result of which, for example, a reduced thermal capacity is also brought about. Irrespective of this, the method step can also simply occur after the shaping step in a sheet metal cutting process, for example in order to cut the pieces of sheet metal to the desired length or width which they are to subsequently have in the exhaust gas treatment component.

In accordance with an additional mode of the invention, a substantially smooth piece of sheet metal is particularly preferably pressed by the at least one fluid stream into at least one countermold, so that the structure of the at least one structured piece of sheet metal is formed. A "countermold" is understood in particular to be dies or swages, matrices or bottom dies, roll forms, toothed wheels, etc. They constitute a type of negative mold into which the piece of sheet metal is pressed using the fluid stream, fits closely against it and in this way permanently assumes the structure. In this context, predominantly plastic deformation of the piece of sheet metal takes place. The countermold then has a surface which corresponds substantially to the desired structure of the piece of sheet metal. Initial tests have shown that in this case a very small degree of deviation in terms of shape can be achieved and the piece of sheet metal therefore assumes the contour of the countermold very precisely. The countermold in this case may be in one piece or a plurality of pieces, with it being possible in the last-mentioned variant in particular to also form undercuts or similar forms of surface structure. The shaping or pressing-in of the piece of sheet metal through the use of the fluid stream also enables such complex countermolds to be reproduced.

In accordance with yet another mode of the invention, at least two fluid streams are used, a first fluid stream bringing about shaping of sheet metal and a subsequent, second fluid stream causing the piece of sheet metal to be fixed with respect to the at least one countermold. In order to ensure that the piece of sheet metal does not lose its defined position with respect to the countermold during the shaping of the sheet metal, it is proposed in this case that the part of the piece of sheet metal which has already been shaped in a structured way remain disposed substantially in a form-locking fashion with respect to the countermold by using a second fluid stream (holding fluid stream). This makes it possible to prevent parts which have already been processed from being pulled back with respect to the first fluid stream. A form-locking connection is one which connects two elements together due to the shape of the elements themselves, as opposed to a force-locking connection, which locks the elements together by force external to the elements.

In accordance with yet a further mode of the invention, it is particularly advantageous if the at least one countermold simultaneously transports the at least one structured piece of sheet metal in a forward feed direction. This means that the countermold itself constitutes the drive or the transporting element for transporting the piece of sheet metal through the device for producing a structure in a piece of sheet metal. In this context the structure which is produced in the piece of sheet metal and the surface of the countermold engage in one another and a relative movement of the surface of the countermold with respect to the fluid distribution device thus also brings about a relative movement of the at least one structured piece of sheet metal with respect to the fluid distribution device. The relative movement may be linear and/or rotational. In other refinements of the method, the transporting of the piece of sheet metal can be supported by the at least one fluid stream or even performed by it. It is also possible for the at least one fluid stream to bring about the forward feed but for the countermold to keep the forward feed rate within a predefinable range by braking the forward feed which is brought about through the use of the at least one fluid stream.

In accordance with yet an added mode of the invention, in a method step which precedes the shaping of sheet metal, a plurality of slits are made in the at least one piece of sheet metal by cutting sheet metal. It is also proposed that the slits be positioned in a controlled fashion with respect to the countermold. This means in other words that it is ensured that the slits which are produced in the piece of sheet metal are also positioned at the desired locations on the countermold when the shaping of the piece of sheet metal takes place. The slits are made in the piece of sheet metal in particular in order to partially limit protrusions, baffle faces or similar projections. It is precisely these protrusions, etc. which are formed by special projections in the countermold that are suitable for this purpose, ensuring that the slit is positioned at the location of the respective projection. This may be ensured, for example, by a special sensor system and/or by coupled drives (mechanical, electrical, electronic data processing drives, etc.) for the device for carrying out the cutting of sheet metal and the device for carrying out the shaping of sheet metal.

In accordance with yet an additional mode of the invention, the at least one structured piece of sheet metal is subjected to a cleaning process after shaping. This cleaning process, which may also, if appropriate, be made up of a plurality of stages, serves preferably primarily to remove components of the fluid stream or contaminating substances which are located on the surface of the piece of sheet metal, etc. The cleaning process can include thermal treatment, chemical treatment and/or mechanical treatment of the piece of sheet metal. Thus, in a water fluid stream, the surface or the piece of sheet metal itself can be dried by using an oven or a blower. Appropriate measures are possible for oil and/or contaminating substances. These may include brushing, etching or other cleaning processes.

In accordance with again another mode of the invention, the at least one structured piece of sheet metal is disposed in such a way that a honeycomb body is formed which has a multiplicity of passages. In this context, a plurality of pieces of sheet metal are preferably stacked, wound and/or rolled together, with at least some of them being structured. This also means that a piece of sheet metal can have regions with a structure and regions without (such) a structure, and that the separate smooth and structured pieces of sheet metal are disposed together to form a honeycomb body. As an alternative or in combination therewith, the at least one structured piece of sheet metal can be combined with further components, for example fiber mats, perforated plates, insulating mats, sealing films, etc.

In particular, two typical structures for metallic honeycomb bodies are differentiated. An early construction, of which German Published, Non-Prosecuted Patent Application DE 29 02 779 A1, corresponding to U.S. Pat. No. 4,273, 681, presents typical examples, is the spiral construction in which substantially one smooth and one corrugated layer of sheet metal are laid one on top of the other and wound in a spiral. In another construction, the honeycomb body is made up of a plurality of alternately disposed smooth and corrugated or differently corrugated layers of sheet metal, with the layers of sheet metal firstly forming one or more stacks which are twisted together. In the process, the ends of all of the layers of sheet metal end up on the outside and can be connected to a housing or casing tube, as a result of which numerous connections are produced that increase the durability of the honeycomb body. Typical examples of those structures are described in European Patent EP 0 245 737 B1, corresponding to U.S. Pat. Nos. 4,832,998, 4,803,189, 4,946, 822 and 4,923,109, or International Publication No. WO 90/03220, corresponding to U.S. Pat. Nos. 5,105,539 and 5,139,844. It has also been known for a long time to equip the layers of sheet metal with additional structures in order to influence the flow and/or bring about cross-mixing between the individual flow passages. See, for example, International Publication No. WO 91/01178, corresponding to U.S. Pat. No. 5,403,559. All of those constructions can be produced with the method proposed herein and the device which is explained later. For this reason, the disclosed contents of the above-mentioned publications are entirely incorporated as part of the description herein and may, if appropriate, be used for explanatory purposes.

What is referred to as the "passage density" is usually used with respect to the number of such passages. This describes how many passages are present per unit cross-sectional area of the honeycomb body. The honeycomb body which is formed preferably has such a passage density of between 100 cpsi ("cells per square inch") and 1600 cpsi. The passages run in this case substantially parallel to one another and form separate, at least partially separated flow paths which are surrounded by passage walls. The piece of sheet metal or the further components can also have openings and/or baffle structures which provide a connection between passages that are disposed next to one another so that the partial flows which are located in the passages in the honeycomb body can be mixed with one another. These passages usually extend substantially linearly from one end face of the honeycomb body to the opposite end side. However, honeycomb bodies having flow paths which have a different profile than this, for example a helical or stepped profile etc. are also known.

In accordance with again a further mode of the invention, in this context, it is particularly advantageous to place the honeycomb body which is formed in this way in contact with a housing and to subsequently carry out a thermal joining process. It is basically possible to place a plurality of such honeycomb bodies in a single housing, but it is also possible for one honeycomb body to be in contact with a plurality of housings or to be at least partially surrounded by a plurality of housings in the radial direction. After the honeycomb body has been disposed in the desired position in the housing, a thermal joining process is proposed herein in order to connect the components of the honeycomb body to one another, and the honeycomb body to the at least one housing. These thermal joining processes can bring about diffusion connections, welded connections and/or brazed connections. In addition, in this context it is possible to produce coatings on the at least one piece of sheet metal or other components of the honeycomb body, which can however additionally or alternatively be carried out in a subsequent coating process.

With the objects of the invention in view, there is also provided a device for producing a structure in a piece of sheet metal. The device comprises a fluid supply device, at least one fluid distribution device providing at least a first fluid stream and a second fluid stream, and at least one countermold.

The device described herein is particularly suitable for producing a structure in a piece of sheet metal according to one of the above-mentioned methods of the invention. The two fluid streams preferably assume different functions in the shaping of the sheet metal in this context. While the first fluid stream, for example, primarily shapes the piece of sheet metal, the second fluid jet preferably mainly serves to retain the shaped piece of sheet metal in the countermold, or press it against the countermold. As a result, a defined position of the piece of sheet metal with respect to the countermold is always ensured so that a precise representation of the structure of the countermold is formed in the piece of sheet metal. The second fluid jet can also be used for subsequent calibration or for a second shaping step (for example in the case of undercuts, etc.). The first fluid stream and the second fluid stream are advantageously produced at least partially simultaneously during the processing, but different starting times and ending times can, if appropriate, be selected while taking into account the form of the piece of sheet metal. It is basically also possible for the fluid distribution device to place similar types of media in contact with the piece of sheet metal, and alternatively the first fluid stream and the second fluid stream can also be formed from different media, or media which are embodied in a different way. The fluid supply device serves to supply the fluid distribution device with the appropriate fluids (water, oil etc.) so that the fluid streams can be produced with the desired parameters. This fluid supply device can include pipelines, pumps, valves, measuring devices, etc. as parts thereof.

In accordance with another feature of the invention, the at least one fluid distribution device has a device for varying at least one of the following parameters with respect to at least the first fluid stream or the second fluid stream:
 a) pressure
 b) flow rate
 c) volume flow
 d) shape.

The device can basically be equipped with a plurality of fluid distribution devices which, for example, act simultaneously one next to the other over a specific width of the piece of sheet metal, or which are disposed one behind the other in the forward feed direction of the piece of sheet metal and, if appropriate, serve to form different structures in the one piece of sheet metal (for example macrostructure/microstructure). At least one of these fluid distribution devices, preferably each of these fluid distribution devices, has such devices for varying the parameters of the fluid streams. The variation can be implemented independently in this case for each individual fluid stream of a fluid distribution device, but a common variation of the first fluid stream and of the second fluid stream is also possible. It is also advantageous to be able to vary at least two of the aforesaid parameters a) to d).

These parameters are preferably monitored during the manufacture of the structured piece of sheet metal and readjusted, if appropriate. The aforesaid device may be part of the fluid distribution device itself, but it is also possible for it to be connected indirectly to the fluid distribution device. The pressure and the volume flow can be monitored and corrected and/or set in this case together with the fluid supply device, for example. The flow rate and the shape of the fluid streams can be influenced, for example, by the shape of the outlet opening of the fluid distribution device. "Shape" of the fluid stream is meant in particular to refer to the manner in which the fluid leaves the fluid distribution device, for example whether the fluid stream tapers, widens, whether it is applied to the piece of sheet metal in a punctiform manner, linearly or over a surface.

In accordance with a further feature of the invention, the at least one fluid distribution device includes at least one nozzle with a gap. Basically, one nozzle can be very different in construction and can be configured in a way which is adapted to the respective purpose of use or the desired shape of the structured piece of sheet metal. It is possible in this context for a "nozzle" to be understood as being, for example, a conically tapering tubular piece for constricting pipelines. A nozzle usually has the property of accelerating the fluid flowing through it, which generally involves a drop in pressure. Nozzles can be used to atomize fluids, for the disperse mingling of various fluids or other components and for other purposes. In this case, preferably a line structure which tapers to form a gap is proposed. This is done with particular regard to the structure that is to be produced and which is also linear in construction due to the usually linear construction of passages. The gap of the nozzle is preferably aligned substantially parallel to the lines of the maximum or minimum points on the structure of the piece of sheet metal or the countermold in order to permit a section of sheet metal to be shaped as uniformly as possible. If structures which differ from this are produced, or if additional structures are formed which are limited locally to specific regions of the piece of sheet metal, other types of nozzles may be used or provided. The gap preferably has a gap width which is less than 1.0 mm, in particular less than 0.5 mm. The length of the gap is determined substantially by the width of the piece of sheet metal which is to be processed. It is usually proposed that pieces of sheet metal with a width of up to 100 mm be processed with a single gap nozzle, which then has a gap length corresponding to the width of the piece of sheet metal.

In accordance with an added feature of the invention, the at least one fluid distribution device has two nozzles which lie opposite a center web and each have a gap. Such a structure permits the gaps of the nozzles to be disposed very closely one next to the other. This permits particularly small structures to be produced in the piece of sheet metal in a way which is non-damaging and easily reproducible since the fluid streams can be aimed directly at adjacent structures of the countermold or of the piece of sheet metal. The two gaps or the two nozzles can be made substantially symmetrical to the center web in this case, but it is also possible for them to be configured in different ways from one another, in particular in the vicinity of the gap, while taking into account their different functions.

In accordance with an additional feature of the invention, the at least one fluid distribution device includes a device for removing the fluid after contact with the piece of sheet metal. Experiments have shown that the fluid stream which is applied to the piece of sheet metal adheres to the surface of the smooth part of the piece of sheet metal and flows along it. In the process, the fluid moves very far away from the processing point, as a result of which disposal or recycling of the fluid is made considerably more difficult. For this reason it is proposed in this case to ensure that the fluid stream is deflected or removed near the processing point. The device necessary for this may, for example, be receiving ducts in the fluid distribution device, baffle plates, blowers, suction lines, etc. These preferably constitute a particular method of guiding the fluid stream through components or parts of the fluid distribution device itself. In this way the use of further active media (for example compressed air, vacuum) can be avoided.

In accordance with again another feature of the invention, the at least one countermold is a rotatable contoured wheel. The contoured wheel is preferably substantially round and can be rotated in a regulated fashion through the use of a drive. The contoured wheel can be configured in one part or in a plurality of parts, for example as a disk configuration. The contoured wheel has the desired surface over its width. The surface ultimately represents a negative mold for the structure which is to be produced in the piece of sheet metal. Contours which are used are prongs, teeth, bolts, projections, etc. that preferably protrude uniformly over the circumference of the contoured wheel.

In accordance with again a further feature of the invention, there is provided a device for driving the contoured wheel in a controlled manner as a function of at least one of the following factors:
  forward feed of the piece of sheet metal;
  supply of a fluid stream by the fluid distribution device;
  monitoring signals of components of the device; and
  shape of the piece of sheet metal.

The dependence of the controlled drive on the forward feed of the piece of sheet metal can be ensured in particular if the contoured wheel is used as a transporting element for the forward feed of the piece of sheet metal itself. That is to say in other words the conical gear is driven in such a way that the desired forward feed of the piece of sheet metal is maintained. This is advantageously carried out intermittently with a clocking frequency of, in particular, more than 20 Hz. It is also possible to make the drive of the conical gear dependent on at least one parameter of the fluid stream, for example the applied flow rate, the applied pressure, the applied volume flow or the shape of the fluid stream. The device can also have sensors, measuring pickups, etc. at various locations and these sense specific measured values and compare them with a reference value. This results in monitoring signals which can, under certain circumstances, result in a variation of the drive. It is also possible for the piece of sheet metal to be configured differently at predefined intervals or in predefined sections, for example when manufacturing different variants with the same device. It may be necessary in this case for different processing times to be required so that different forward feed rates of the piece of sheet metal or rotational speeds of the contoured wheel have to be set as a function of the shape of the piece of sheet metal. The device is preferably able to control or regulate the drive of the contoured wheel as a function of at least two of the above-mentioned factors, preferably even of all the factors.

In accordance with again an added feature of the invention, the device is combined with a device for cutting sheet metal. This also means in particular that the drives of the device for cutting sheet metal and the drives of the contoured wheel are synchronized with one another so that slits, openings and the like can be formed in the piece of sheet metal to be structured at the desired location on the contoured wheel or the countermold if they are given the desired structure.

In accordance with a concomitant feature of the invention, there is provided at least one sensor and at least one evaluation unit. Such sensors can be used for functional monitoring or for localizing working results. The signals which are generated with the at least one sensor are preferably combined in a superordinate evaluation unit which, for example, matches the drives of the different devices to one another.

Other features which are considered as characteristic for the invention are set forth in the appended claims, noting that the features specified in the claims can be combined with one another as well as with the features in the description, in any appropriate manner without departing from the inventive concept.

Although the invention is illustrated and described herein as embodied in a method and a device for fluid-shaping of sheet metal, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF DRAWINGS

FIG. 5A is a fragmentary, partly broken-away, perspective view and FIG. 5B is an enlarged view of a portion V of FIG. 5A, showing an exemplary embodiment of an exhaust gas treatment component; and FIGS. 6A-6D are perspective views of various exemplary embodiments of structures in a piece of sheet metal.

DESCRIPTION OF THE PREFERRED EMBODIMENTS

Figure 1:
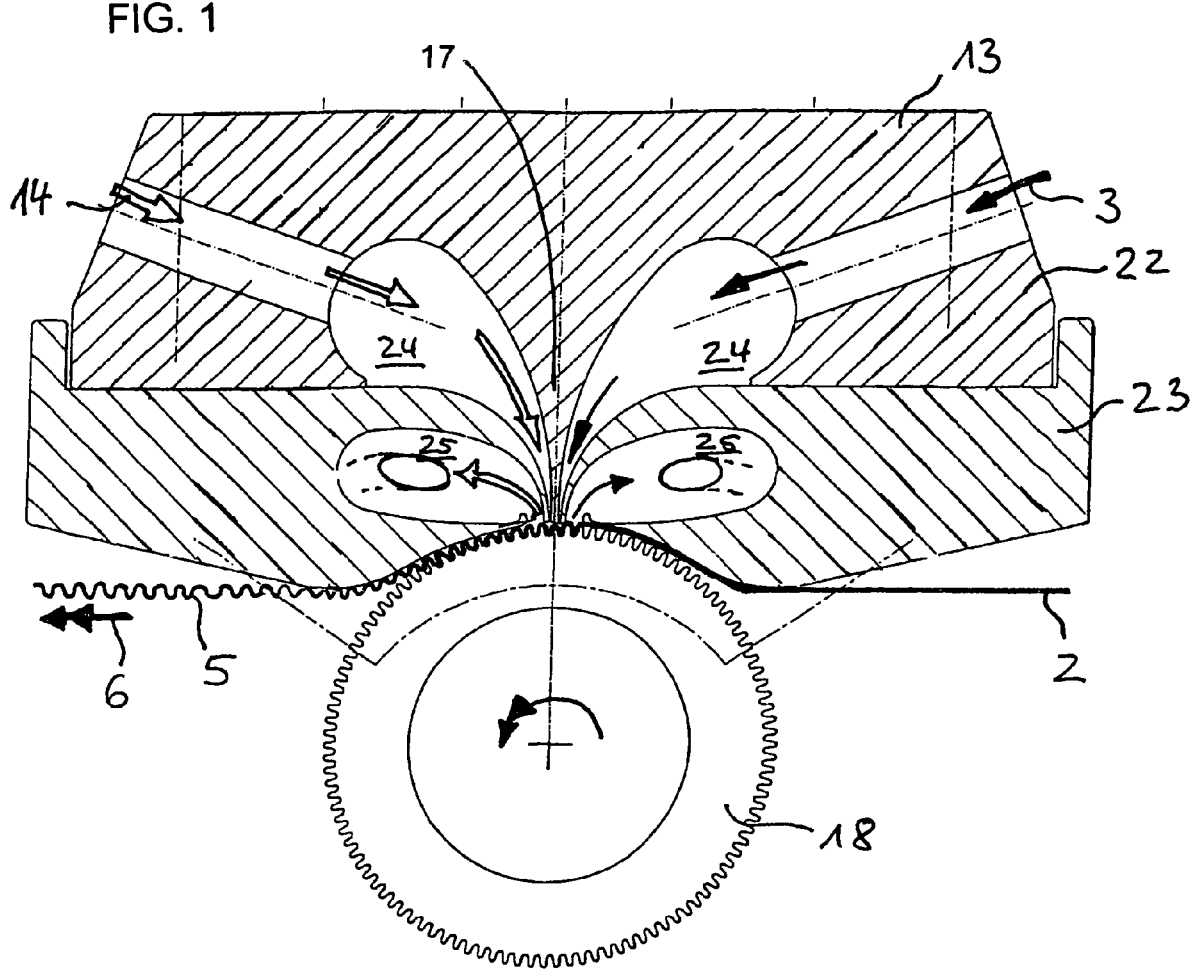
FIG. 1 is a diagrammatic, partially cross-sectional view of an exemplary embodiment of a fluid distribution device for producing a structure in a piece of sheet metal.
Figure 2:
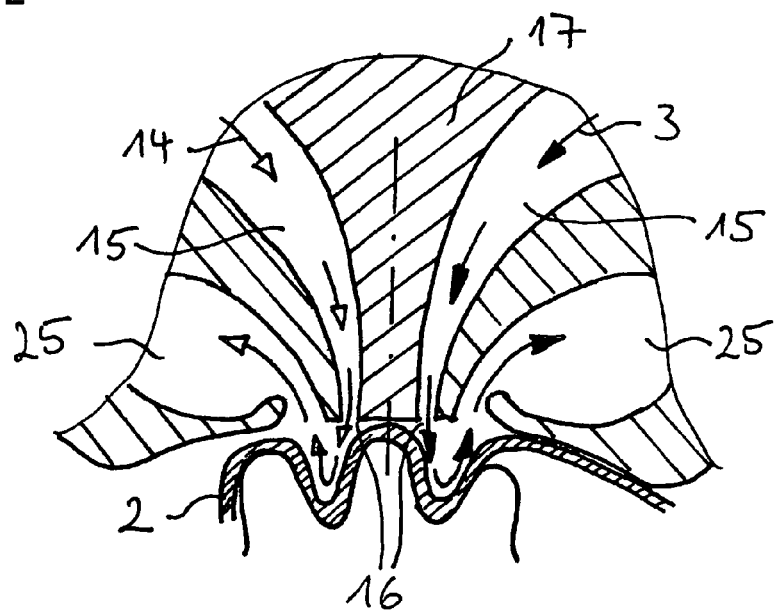
FIG. 2 is an enlarged, fragmentary, cross-sectional view of the fluid distribution device illustrated in FIG. 1.

Referring now to the figures of the drawings in detail and first, particularly, to FIG. 1 thereof, there is seen a diagrammatic, partially sectional view of a possible embodiment of a fluid distribution device 13 for producing a piece 2 of sheet metal with a structure 5. The fluid distribution device 13 is formed in two parts in this case and has an upper part 22 and a lower part 23. The upper part 22 is provided with two inflow ducts 24. A first inflow duct 24 is provided for a first fluid stream 3 (indicated by black arrows), and a second inflow duct 24 is provided for a second fluid stream 14 (indicated by white arrows). The two inflow ducts 24 extend substantially symmetrically with respect to a center web 17. In the embodiment of the fluid distribution device 13 which is illustrated in this case, the inflow ducts 24 are also partially bounded by the lower part 23. As is seen in FIG. 2, regions of the lower part 23 form gap nozzles 15 with the center web 17 of the upper part 22. The piece 2 of sheet metal is conducted past these gap nozzles 15 and the fluid streams 3, 14 are applied thereto. In the process, the piece 2 of sheet metal is pressed into a countermold or counter form 4, which is represented in this case as a contoured wheel 18. In this case, the fluid distribution device 13 is disposed on one side of the piece 2 of sheet metal and the countermold, configured in this case as a contoured wheel 18, is disposed opposite the fluid distribution device 13 on the other side. The contoured wheel 18 turns intermittently, giving rise to a forward feed direction 6 of the piece 2 of sheet metal in the process.

During the processing, the fluid streams 3, 14 flow toward the piece 2 of sheet metal and press it into the contour of the contoured wheel 18, with the fluid streams 3, 14 being deflected in terms of their direction of flow. After contact with the piece 2 of sheet metal, the flow streams flow into outlet ducts 25 which are provided in the lower part 23 of the fluid distribution device 13. The fluid streams are conditioned again starting from these outlet ducts 25 and can thus be fed again to the fluid distribution device 13 in order to process a piece 2 of sheet metal.

FIG. 2 is a fragmentary, diagrammatic view showing the nozzles 15, which are each formed with a gap 16. As illustrated, the first fluid stream 3 (black arrows) and the second fluid stream 14 (white arrows) initially flow toward the center web 17 and continue on in the direction of the respective gap 16. There the fluid streams 3, 14 emerge and come into contact with the piece 2 of sheet metal disposed underneath. In the process, they press the piece 2 of sheet metal into the contour of the contoured wheel 18 disposed opposite the fluid streams, with the piece 2 of sheet metal at least partially experiencing plastic deformation and assuming the desired structure 5 which corresponds substantially to the contour of the contoured wheel 18. Due to the contour or the structure 5, the fluid streams are deflected, during which process they are directed into their respective outlet duct 25. The nozzles 15 and the outlet ducts 25 are disposed so as to correspond to the flow deflections which are brought about by the structure 5 and the countermold 4. In this way, a very large part of the fluid stream 3, 14 which is used can be removed again directly after contact with the piece 2 of sheet metal.

Figure 3:
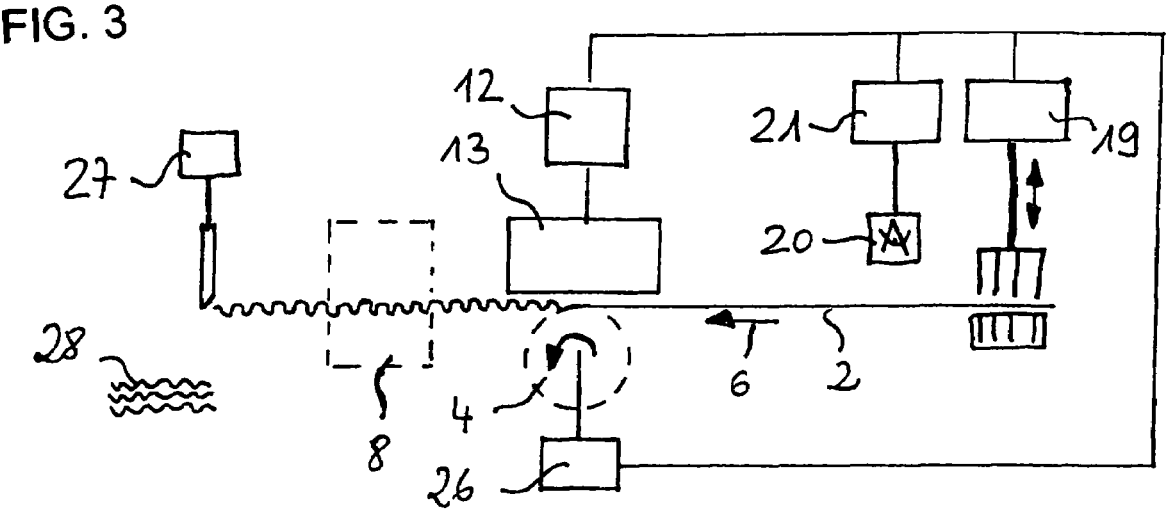
FIG. 3 is a block diagram of an embodiment of a device for carrying out a method for producing a structure in a piece of sheet metal.

FIG. 3 is a diagrammatic view of a possible construction of a fabrication system for manufacturing exhaust gas treatment components, which also includes the device according to the invention for producing a structure 5 in a piece 2 of sheet metal. The piece 2 of sheet metal is initially fed in the forward feed direction 6 to a sheet metal cutting device 19. The forward feed of the piece 2 of sheet metal is produced in this case by the countermold 4. The sheet metal cutting device 19 produces slits 7 (shown in FIG. 4), openings 40 (shown in FIG. 6D) or other cutouts in the material of the piece 2 of sheet metal. The piece 2 of sheet metal is subsequently conducted past a sensor 20 which monitors, for example, the functionality of the sheet metal cutting device 19. Signals which are acquired with the sensor 20 are passed on to an evaluation unit 21.

The piece 2 of sheet metal is then moved on in the direction of the fluid distribution device 13 by rotating the countermold 4. For this purpose, the countermold 4 is equipped with a drive 26 which permits intermittent forward feed of the piece 2 of sheet metal. The fluid distribution device 13 is provided with the fluid which is necessary to process the piece 2 of sheet metal by a fluid supply or conditioning device 12. The fluid presses the previously smooth piece 2 of sheet metal into the contour or countermold 4 so that the piece 2 of sheet metal experiences plastic deformation.

The piece 2 of sheet metal which is now structured is transported on to a cleaning device 8 where, for example, residues of the fluid and contaminating substances are removed. The cleaning device 8 may be constructed as a continuous oven, a blower or a combination of both. The cleaned and dried structured piece 2 of sheet metal is then finally fed to a cutting device 27 which cuts individual foils 28 from the piece of sheet metal that is configured as a strip. In the illustrated system, the evaluation unit 21 assumes the function of regulating various components, in particular the fluid supply device 12, the sheet metal cutting device 19 and the drive 26 of the countermold 4, which is at the same time configured in this case as a transporting element.

Figure 4:
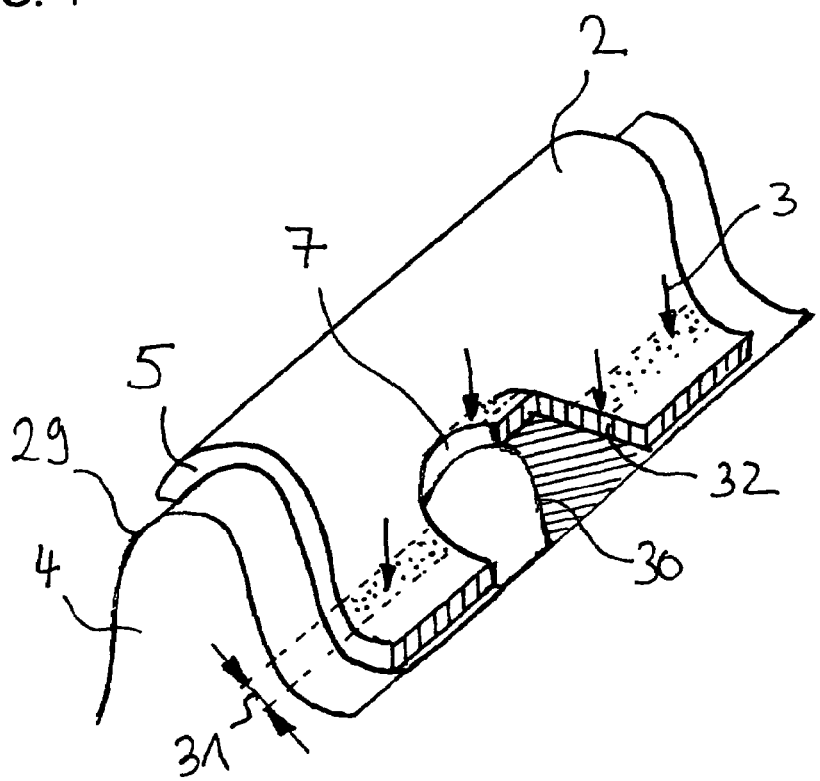
FIG. 4 is a further enlarged, fragmentary, perspective view of a contact region between a countermold and a piece of sheet metal.

FIG. 4 is a fragmentary, diagrammatic view of an exemplary embodiment of a countermold 4 and a piece 2 of sheet metal which fits snuggly against or is adapted thereto. The countermold 4 has, on one hand, a primary contour 29 and a secondary contour or structure 30 which is superimposed thereon. The piece 2 of sheet metal has firstly been slit with a sheet metal cutting device 19 so that slits 7 are formed in internal regions of the piece 2 of sheet metal. The slits 7 are disposed so as to correspond to the secondary contours 30 of the countermold 4. The first fluid stream 3, which decisively brings about the shaping of the piece 2 of sheet metal in this case, is configured with a linear shape and has a width 31 which is preferably less than 0.5 mm. Due to the impinging of the first fluid stream 3 onto the piece 2 of sheet metal, on one hand a structure 5 which corresponds to the primary contour 29 is formed, but in addition a protrusion 32 is also formed and is shaped by providing the slit 7 and the secondary contour 30.

FIG. 5A shows an exemplary embodiment of an exhaust gas treatment component 1 as can ultimately be produced after the method has been carried out. The exhaust gas treatment component 1 has a housing 11 which at the same time includes three honeycomb bodies 9 that are disposed one behind the other and spaced apart from one another. The honeycomb bodies 9 have a multiplicity of passages, cells or channels 10 through which exhaust gas can flow. The passages 10 are formed by a structured piece 2 of sheet metal and a smooth strip 33. It is possible from the enlarged view of FIG. 5B to see that the smooth strip 33 is configured as a porous filter layer. In addition, a coating 34 is provided both on the smooth strip 33 and on the piece 2 of sheet metal. In this case, the piece 2 of sheet metal has a sheet metal thickness 35 of less than 110 μm.

FIGS. 6A-6D are diagrammatic perspective views of four different examples of structures 5 of the piece 2 of sheet metal. The variant which is illustrated in FIG. 6A exhibits a sinusoidal-like structure 5 which can be described by a width 36 and a height 37. Relatively narrow structures in which the ratio of height to width is in the region of less than 2, in particular in the region of 1.5 to 1.3, are preferred in this case.

FIG. 6B illustrates a structure 5 on which a second, so-called microstructure 38 is superimposed. In this case, the structure 5 and the microstructure 38 are formed substantially perpendicularly with respect to one another but they can also extend obliquely with respect to one another.

The structure 5 of the variant shown in FIG. 6C has a substantially rectangular profile. The variant according to FIG. 6D has a so-called omega structure which has additional openings 40 and undercuts 39 that cannot usually be readily produced by rolling methods.

The method and the device according to the invention described herein permit various embodiments of structures to be formed in pieces of sheet metal in a particularly simple and cost-effective fashion. These fabrication steps themselves can fulfill the requirements for the manufacture of exhaust gas treatment components, something which has previously not been taken into consideration.

I claim:

1. A method for manufacturing an exhaust gas treatment component, the method comprising the following steps:

provided at least one piece of sheet metal based on iron and including at least one of the elements from the group consisting of chromium, nickel, and aluminum, the piece of sheet metal having a width; and structuring the at least one piece of sheet metal with a structure shaped across the entire width by shaping with at least one fluid stream.

2. The method according to claim 1, wherein the at least one fluid stream has at least one component selected from the group consisting of:
water,
oil,
particles, and
additives.

3. The method according to claim 1, which further comprises carrying out the shaping step intermittently.

4. The method according to claim 1, which further comprises, before the shaping step, subjecting the at least one piece of sheet metal to a step including sheet metal cutting.

5. The method according to claim 1, which further comprises carrying out the shaping step by pressing a substantially smooth piece of sheet metal with the at least one fluid stream into at least one countermold to form a structure in the at least one piece of sheet metal.

6. The method according to claim 5, wherein the at least one fluid stream includes at least first and second fluid streams, and the shaping step is carried out by bringing about shaping of the at least one piece of sheet metal with the first fluid stream and subsequently causing the at least one piece of sheet metal to be fixed relative to the at least one countermold with the second fluid stream.

7. The method according to claim 5, which further comprises simultaneously transporting the at least one structured piece of sheet metal in a forward feed direction with the at least one countermold.

8. The method according to claim 5, which further comprises, before the step of shaping the at least one piece of sheet metal, forming a plurality of slits in the at least one piece of sheet metal by sheet metal cutting, and positioning the slits relative to the countermold in a controlled manner.

9. The method according to claim 1, which further comprises subjecting the at least one structured piece of sheet metal to a cleaning process after the shaping step.

10. The method according to claim 1, which further comprises forming the at least one structured piece of sheet metal into a honeycomb body having a multiplicity of passages.

11. The method according to claim 10, which further comprises bringing the honeycomb body into contact with a housing and subsequently carrying out a thermal joining process.

\* \* \* \* \*